US010912884B2

(12) United States Patent
Brandenburg et al.

(10) Patent No.: US 10,912,884 B2
(45) Date of Patent: Feb. 9, 2021

(54) INFUSION SET

(71) Applicant: ViCentra B.V., Utrecht (NL)

(72) Inventors: Allen E. Brandenburg, Dripping Springs, TX (US); George R. Lynch, Coppell, TX (US); Bret W. Price, Hondo, TX (US); David C. Cocke, San Antonio, TX (US)

(73) Assignee: ViCentra B.V, Utrecht (NL)

(*) Notice: Subject to any disclaimer, the term of this patent is extended or adjusted under 35 U.S.C. 154(b) by 569 days.

(21) Appl. No.: 15/739,002

(22) PCT Filed: Jul. 21, 2016

(86) PCT No.: PCT/EP2016/067457
§ 371 (c)(1),
(2) Date: Dec. 21, 2017

(87) PCT Pub. No.: WO2017/013227
PCT Pub. Date: Jan. 26, 2017

(65) Prior Publication Data
US 2018/0344926 A1    Dec. 6, 2018

Related U.S. Application Data

(60) Provisional application No. 62/195,539, filed on Jul. 22, 2015, provisional application No. 62/195,579, filed on Jul. 22, 2015.

(51) Int. Cl.
*A61M 5/158*        (2006.01)
*A61M 5/142*        (2006.01)

(52) U.S. Cl.
CPC ........ *A61M 5/158* (2013.01); *A61M 5/14248* (2013.01); *A61M 2005/1585* (2013.01);
(Continued)

(58) Field of Classification Search
CPC .. A61M 5/007; A61M 5/14546; A61M 25/10; A61M 25/10182; A61M 25/1011;
(Continued)

(56) References Cited

U.S. PATENT DOCUMENTS 5,257,980 A    11/1993  Van Antwerp et al.
7,214,207 B2*   5/2007  Lynch ................... A61M 5/158
                                                 604/93.01
(Continued)

FOREIGN PATENT DOCUMENTS

CN    201578690 U    9/2010
EP    2 692 374 A1   2/2014
(Continued)

OTHER PUBLICATIONS

Jan. 30, 2017 Transmittal of International Search Report and Written Opinion of International Searching Authority for PCT/EP2016/067457.
(Continued)

*Primary Examiner* — Manuel A Mendez
(74) *Attorney, Agent, or Firm* — Hahn Loeser & Parks LLP

(57) ABSTRACT

The present application relates to an infusion set (80). The infusion set (80) has a base (90) for mounting on a user, and a connector (100) which engages with the base (90) to form a flow path between the connector (100) and a cannula mountable on the base (90). The connector (100) is configured to be selectably mountable to the base (90) in at least two predetermined mounting orientations. The present application also relates to an infusion set base (90), an infusion set connector (100), an infusion set cannula, and a method of assembling an infusion set (80).

14 Claims, 13 Drawing Sheets

(52) U.S. Cl.
 CPC ............... *A61M 2005/1586* (2013.01); *A61M 2005/1587* (2013.01)

(58) Field of Classification Search
 CPC ....... A61M 5/19; A61M 25/104; A61B 17/22; A61F 7/12
 See application file for complete search history.

(56) References Cited

U.S. PATENT DOCUMENTS

| | | |
|---|---|---|
| 2001/0053889 A1 | 12/2001 | Marggi et al. |
| 2003/0216686 A1 | 11/2003 | Lynch et al. |
| 2005/0101910 A1 | 5/2005 | Bowman et al. |
| 2005/0101933 A1 | 5/2005 | Marrs et al. |
| 2005/0215979 A1 | 9/2005 | Kornerup et al. |
| 2008/0243085 A1 | 10/2008 | DeStefano |

FOREIGN PATENT DOCUMENTS

| | | |
|---|---|---|
| EP | 2 712 642 A1 | 4/2014 |
| WO | WO 2011/080699 A2 | 7/2011 |
| WO | WO 2013/086463 A1 | 6/2013 |

OTHER PUBLICATIONS

Feb. 25, 2020 Official Communication in connection with CN 2016 8004 3120.7.

\* cited by examiner

INFUSION SET

The present application is a § 371 submission of international application no. PCT/EP2016/067457, filed 21 Jul. 2016 and entitled An Infusion Set, which was published in the English language on 26 Jan. 2017 with publication no. WO 2017/013227, and which claims the benefit of the filing dates of U.S. Ser. No. 62/195,539 filed on 22 Jul. 2015 and US Ser. No. 62/195,579 filed on 22 Jul. 2015, the contents of which are incorporated herein by reference.

FIELD OF THE INVENTION

The present invention relates to an infusion set. In particular, the present invention relates to an infusion set having a base and a connector. The present invention also relates separately to an infusion set base and an infusion set connector. The present invention also relates to an infusion set cannula and a method of assembling an infusion set.

BACKGROUND OF THE INVENTION

Subcutaneous medicament delivery devices are known. Such devices comprise an infusion set. An infusion set typically comprises a base, a connector and a cannula.

Infusion sets are an assembly which provides a comfortable secure means of administering a medication like but not limited to insulin from an infusion pump to a patient over a period of several days.

Infusion sets are commonly used by patients needing continuous or intermittent doses of medication like insulin. These medications work best when delivered to the subcutaneous fat for absorption. The infusion sets are applied to the skin of the patient usually with an introducer needle that penetrates the skin and passes into the subcutaneous fat. The needle is inside the body of the cannula so that when the needle is removed, the cannula tip is situated in the subcutaneous fat. An adhesive is usually used to hold the set in place. The set may typically be worn for up to 3 days before needing to replace it with a new set. The medication is supplied by an infusion pump device which is usually programmable to deliver medication as needed based on the activities of the patient.

Infusion sets are typically constructed of several components including a rigid plastic housing attached to a flexible, adhesive backed dressing. The housing holds the cannula and a seal and provides the method of attaching the connector from the tubing which leads to the infusion pump. There are several components which add manufacturing complexity and the need to seal several parts together to provide a sealed flow path through which the medication flows to the patient. Additionally, the hard edge of the housing can dig into the patient's skin and create discomfort.

A problem with known infusion sets is that once the infusion set base is attached to the patient's skin, the routing of the tubing extending from the infusion set is fixed. This may lead to uncomfortable tugging if the tubing extends in an undesirable orientation. One approach at solving this problem is to provide a connector which is rotatably mounted to the base. However, such an arrangement may lead to twisting of the tubing and may be difficult to provide the necessary sealing.

SUMMARY OF THE INVENTION

According to one aspect of the invention, there is provided an infusion set comprising a base; and a connector configured to engage with the base to form a flow path between the connector and a cannula mountable on the base, wherein the connector is configured to selectably mount to the base in at least two predetermined mounting orientations.

The base may further comprise a cannula receiving arrangement. The connector may be configured to align with the cannula receiving arrangement to form the flow path when mounted irrespective of the selected mounting orientation.

The base may comprise a first latch engaging arrangement and a second latch engaging arrangement. The connector may comprise a first latch which is configured to engage with the first latch engaging arrangement to selectably mount the connector in a first predetermined mounting orientation, and is configured to engage with the second latch engaging arrangement to selectably mount the connector in a second predetermined mounting orientation.

The connector may comprise a second latch which is configured to engage with the second latch engaging arrangement to selectably mount the connector in the first predetermined mounting orientation, and may be configured to engage with the first latch engaging arrangement to selectably mount the connector in the second predetermined mounting orientation.

The infusion set may further comprising a cannula.

According to another aspect of the invention, there is provided an infusion set base comprising a mounting arrangement for mounting an infusion set connector to the base to form a flow path between the connector and a cannula mountable on the base, wherein the mounting arrangement is configured to engage with the connector to enable the connector to be selectably mounted to the base in at least two predetermined mounting orientations.

The infusion set base may further comprise a cannula receiving arrangement, wherein the mounting arrangement is configured to align the connector with the cannula receiving arrangement when the connector is mounted on the base.

The mounting arrangement may be symmetrical about at least one line of symmetry extending through the cannula receiving arrangement.

The mounting arrangement may comprise a first latch engaging arrangement configured to engage with a first latch on the connector to selectably mount the connector in a first predetermined mounting orientation, and a second latch engaging arrangement configured to engage with the first latch on the connector to selectably mount the connector in a second predetermined mounting orientation.

The second latch engaging arrangement may be configured to engage with a second latch on the connector when the first latch engaging arrangement is engaged with the first latch on the connector. The second latch engaging arrangement may be configured to engage with the first latch on the connector when the first latch engaging arrangement is engaged with the second latch on the connector.

The infusion set base may further comprise a pocket for at least partially receiving the connector, and the first latch engaging arrangement is a first receptacle extending from the pocket.

The second latch engaging arrangement may be a second receptacle extending from an opposing side of the pocket to the first latch engaging arrangement.

The first latch engaging arrangement may be at least substantially identical to the second latch engaging arrangement.

The infusion set base may further comprise a rigid central portion configured to engage with the infusion set connector to form a flow path between the connector and a cannula mountable on the base, and a flexible peripheral portion configured to flex to the contours of a user's skin when applied to a user, wherein the rigid central portion and flexible peripheral portion are integrally formed.

According to another aspect of the invention, there is provided an infusion set connector comprising a connecting arrangement for mounting the connector to an infusion set base to form a flow path between the connector and a cannula mountable on the base, wherein the connecting arrangement is configured to engage with the base to enable the connector to be selectably mounted to the base in at least two predetermined mounting orientations.

The infusion set connector may further comprise a flow channel forming part of the flow path between the connector and the cannula mountable on the base, wherein the connecting arrangement may be configured to align the flow channel with the cannula when the connector is mounted on the base.

The connecting arrangement may be at least substantially symmetrical about at least one line of symmetry extending through the flow channel.

The infusion set connector may further comprise a body with a sealing surface for sealing with the cannula.

The connecting arrangement may comprise a first latch configured to engage with a first latch engaging arrangement on the base to selectably mount the connector in a first predetermined mounting orientation, and a second latch configured to engage with the first latch engaging arrangement on the base to selectably mount the connector in a second predetermined mounting orientation.

The second latch may be configured to engage with a second latch engaging arrangement on the base when the first latch is selectably engaged with the first latch engaging arrangement, and the second latch may be configured to engage with the first latch engaging arrangement when the first latch is selectably engaged with the second latch engaging arrangement.

The first latch may be fixed relative to the base.

The first latch is on at least one fixed arm extending from the body.

The second latch may be movable relative to the base.

The infusion set connector may further comprise at least one resiliently deflectable arm which is deflectable relative to the body, and the second latch may be on the at least one deflectable arm.

The second latch may comprise at least two latch tabs protruding from the releasable arm.

The at least one resiliently deflectable arm may comprise first and second deflectable arms. The second latch may comprise a first latch tab on the first deflectable arm and a second latch tab on the second deflectable arm.

According to another aspect of the invention, there is provided an infusion set cannula comprising a resiliently deformable hub portion configured to be engaged with a base of an infusion set, a stem portion extending from the hub portion, wherein the hub portion and stem portion are integrally formed.

The infusion set cannula may further comprise a flow conduit defined by the hub portion and stem portion. The inflow to the flow conduit may be defined by the hub portion.

The hub portion may comprise a circumferentially extending arched section.

The arched section may be arched in a radial direction away from the inflow.

The arched section may comprise a circumferentially extending peak. It may be configured to deform against a sealing surface of a connector when the arched section is axially compressed.

The arched section may further comprise a peripheral rim. The peripheral rim may be configured to distend radially outwardly when the arched section is axially compressed.

The thickness of the arched section may converge from the circumferentially extending peak to the peripheral rim.

According to another aspect of the invention, there is provided an infusion set comprising an infusion set base, an infusion set connector and an infusion set cannula as recited above, wherein the hub portion is configured to be axially compressed between the base and the connector.

The base may comprise a recess configured to receive a hub portion of the cannula. The connector may comprise a sealing surface. The distance between the base of the recess and the sealing surface when the infusion set is assembled may be configured to be less than the thickness of the hub portion.

The recess may comprise an undercut in a sidewall configured to receive part of the hub portion.

The base may be an infusion set base as recited above.

The connector may be an infusion set connector as recited above.

According to another aspect of the invention, there is provided an infusion set comprising an infusion set base as recited above, and an infusion set connector as recited above.

According to another aspect of the invention, there is provided an infusion set as recited above further comprising an infusion set cannula as recited above.

According to another aspect of the invention, there is provided an infusion set base comprising a rigid central portion configured to engage with an infusion set connector to form a flow path between the connector and a cannula mountable on the base, and a flexible peripheral portion configured to flex to the contours of a user's skin when applied to a user, wherein the rigid central portion and flexible peripheral portion are integrally formed.

The rigid central portion and flexible peripheral portion may be integrally formed from a single material.

The infusion set base may further comprise an intermediate portion which converges in thickness from the central portion to the peripheral portion.

According to another aspect of the invention, there is provided a method of assembling an infusion set comprising a base; and a connector configured to engage with the base to form a flow path between the connector and a cannula mountable on the base, wherein the connector is configured to selectably mount to the base in at least two predetermined mounting orientations, the method comprising assembling a cannula with the base, and selectably mounting the connector to the base in one of the at least two predetermined mounting orientations.

BRIEF DESCRIPTION OF THE DRAWINGS

Embodiments of the invention will now be described with reference to the accompanying drawings, in which.

DETAILED DESCRIPTION OF EMBODIMENT(S)

Figure 1:
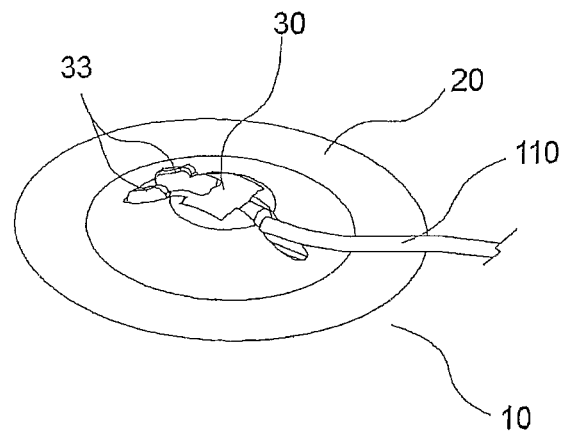
FIG. 1 is an upper perspective view of an assembled infusion set.

FIG. 1 shows an assembled infusion set 10. The infusion set 10 is a flexible infusion set, but in embodiments the infusion set 10 is inflexible. The infusion set 10 comprises a base 20 and a connector 30. At least part of the base 20 is flexible, although the base 20 may be inflexible.

The connector 30 has release arms 33. The release arms 33 act as deflectable arms. In FIG. 1, two release arms 33 are shown. The number of release arms may differ, for example the arrangements shown in FIG. 13 and FIG. 18 each have a single release arm. It will be understood that features from each arrangement are applicable to other arrangements. For example, the arrangement of FIG. 18 may be provided with two release arms.

A tubing 110 is provided on the connector 30. The tubing 110 is bonded on the connector 30. The tubing 110 mounts to the connector 30 at a tubing end.

Figure 2:
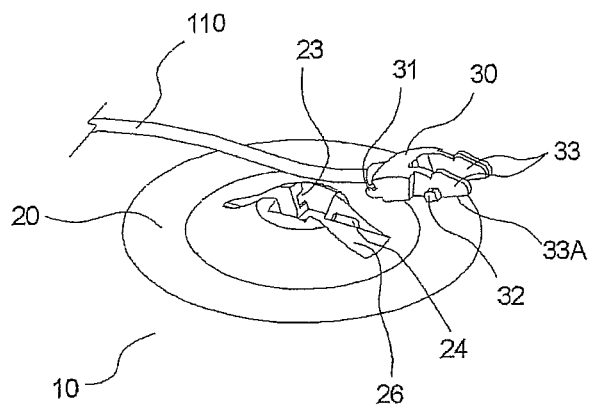
FIG. 2 is an exploded upper perspective view of the infusion set of FIG. 1 with a connector disconnected from a base.

In FIG. 2, the infusion set 10 is shown with connector 30 disconnected from the base 20. It will be noted that the connector 30 is inserted into the base 20 by the tubing end of the connector 30 and then pivoted down to latch in place. This arrangement restricts tugs on the tubing 110 from deforming the release arms 33 and causing accidental disconnection of the connector 30.

Figure 3:
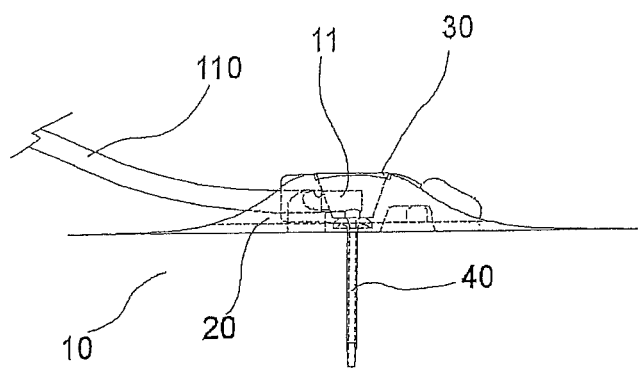
FIG. 3 is a side view of the infusion set of FIG. 1 and FIG. 2 with the connector, base, a cannula and a tubing.
Figure 4:
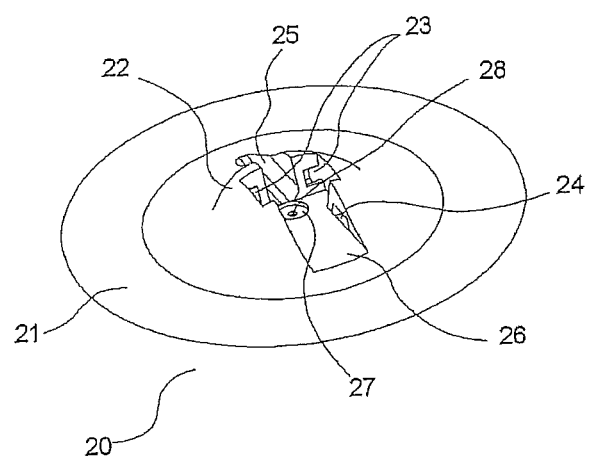
FIG. 4 is an upper perspective view of the base of the infusion set shown in FIG. 1.

FIG. 3 shows the assembled infusion set from the side. A cannula 40 is mounted to the base 20. The fluid path 11 is a sealed flow path from the tubing 110 through the connector 30 to the cannula 40. Fluid path 11 is a continuous sealed channel for the unrestricted flow of medication from a dispensing device (not shown), such as an infusion pump, connected to tubing 110 through the connector 30 and cannula 40.

The base 20 is molded from a material like silicone or flexible PVC. It includes a flat bottom surface for attachment to the patient by adhesive. An outer thin area 21 of the base 20 has a minimised thickness to utilize the flexibility of the material to conform to the curvature of the patient's skin. The thin area 21 is a peripheral portion. The peripheral portion is flexible. The base 30 has a transitional portion in which the thickness of the base 30 gradually increases from the peripheral section 21 to a thick area 22. The rigidity of the central portion decreases in a radially outward direction. The thick area 22 is a central portion. The thick area 22 is rigid. The central portion 22 of the base 20 is configured to receive the cannula 40 and a connecting arrangement of the connector for insertion and retention of the connector 30. The central portion 22 provides an increased stiffness to hold the other components securely.

The peripheral portion 21 of the base 20 comprises approximately half of the outer area of the base 20. The surface gradually slopes to the central portion 22 at the centre of base 20. The central portion 22 provides an increased stiffness for features such as a mounting arrangement of the base 20. A pocket is formed in the base 20 for at least partially receiving the connector 30. A channel distends the central portion 22. The channel comprises a tubing channel 25 and a release arms channel 26. The tubing channel 25 and a release arms channel 26 extend from the pocket.

The base 20 comprises a cannula receiving arrangement. The cannula receiving arrangement comprises a recess 27 to receive the cannula 40 and an opening 28 to permit a stem 45 of the cannula 40 to extend through base 20.

The mounting arrangement comprises first and second receptacles 23, 24. The receptacles 23, 24 extend from the pocket. The receptacles 23, 24 are indents in the sidewalls of the pocket, although alternative arrangements are envisaged.

The flexible peripheral section 21 allows the base 20 to flex and conform to the patient but, rather than a hard edge of the housing creating a pressure point, the gradual increase in thickness to the central portion 22 provided by the transitional portion makes a smooth transition to the central portion 22 of the base 20 where the features for attachment of the other components are located. This central portion 22 provides an increased strength and stiffness for the mounting arrangement. It is the basic nature of the flexible materials used to mold the base 20 that their stiffness increases in direct proportion to their thickness. Several materials are available for this application included but not limited to silicone and flexible PVC and the compounds can be formulated to be softer or stiffer to provide the right combination of strength and adaptability to the patient's skin.

Figure 5:
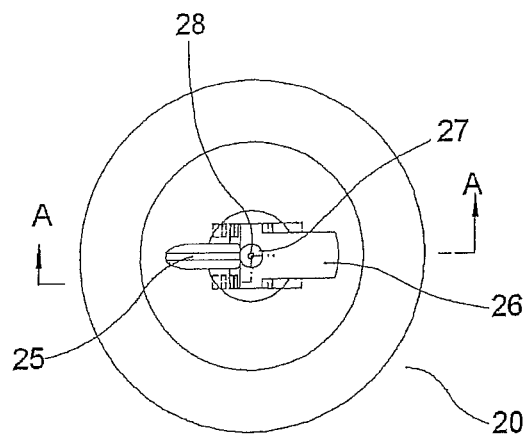
FIG. 5 is a top view of the base shown in FIG. 4.
Figure 6:
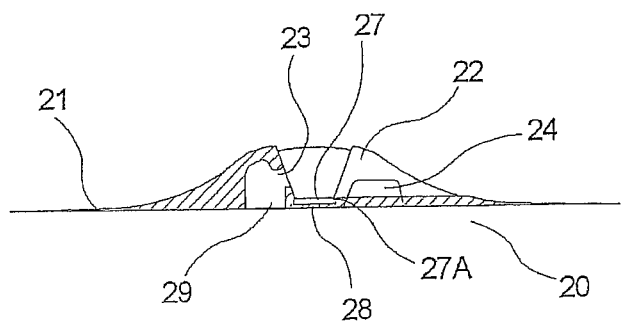
FIG. 6 is a cross-sectional side view of the base shown in FIG. 4.

Referring to FIG. 5 and FIG. 6, the base 20 is shown having the recess 27, the opening 28, a tubing channel 25, and release arm channel 26.

A cavity 29 is formed by a bypass core that creates the first receptacle 23 during molding of base 20. The use of by-pass cores make the molding of the base 20 simpler and avoids moving parts and makes the molds last longer. Second receptacle 24 is molded in a similar manner. The surface of base 20 slopes gradually from the peripheral portion 21 to the central portion 22.

Recess 27 contains undercut edges 27A to facilitate a press fit assembly of tapered edge 43 of the cannula 40. The tapered edge 43 defines a peripheral edge of the cannula 40. As such, the base 20 includes the undercut 27A to help retain the cannula 40. This feature makes a snap assembly possible and eliminates extra parts usually required to hold the cannula 40 in place. The compressive action acting on the cannula 40 acts to further secure the peripheral edge of the cannula 40.

An alternate method of assembly would be to use a small amount of adhesive to help hold the cannula 40 in place. The flexible material used to mold the base 20 also makes it possible to mold the undercut 27A. Opening 28 permits stem 45 of the cannula 40 to pass through base 20.

Figure 7:
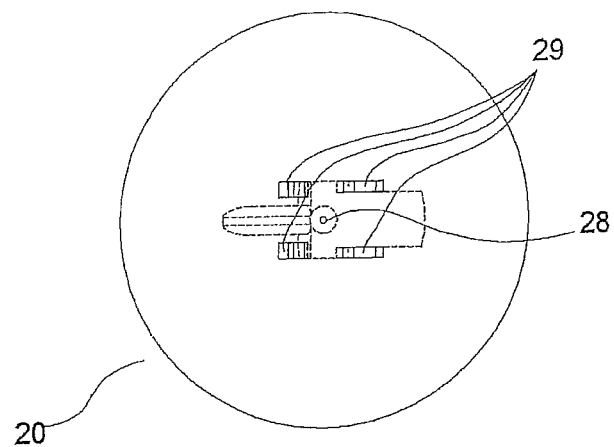
FIG. 7 is a bottom view of the base shown in FIG. 4.

FIG. 7 shows the bottom surface of the base 20 where adhesive is attached to hold the assembled infusion set 10 to the patient. The cavities 29 for the by-pass cores and the opening 28 for the cannula stem 45 are also shown in this view.

Figure 8:
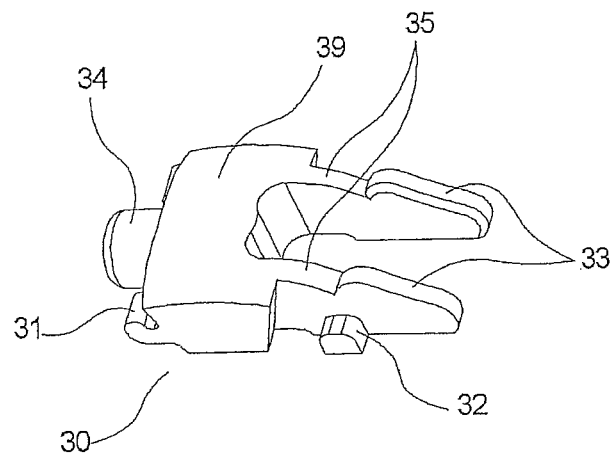
FIG. 8 is an upper perspective view of the connector of the infusion set shown in FIG. 1.

In FIG. 8 the connector 30 is shown. The connector has a body 39. The body is generally symmetrical. The body 39 has a sealing surface 38. The connector 30 has a connecting arrangement. The connecting arrangement comprises first latch tabs 31 and second latch tabs 32. The first and second latch tabs 31, 32 differ in configuration in this embodiment. The connector 30 also has a tubing boss 34. Each release arm 33 is joined to body 39 by a springy hinge area 35, also known as a resilient hinge member. The springy hinge areas 35 act as a resilient arrangement to resiliently connect each of the release arms 33 with the body 39. That is, the release arms 33 are resiliently mounted on the body 39.

Figure 9:
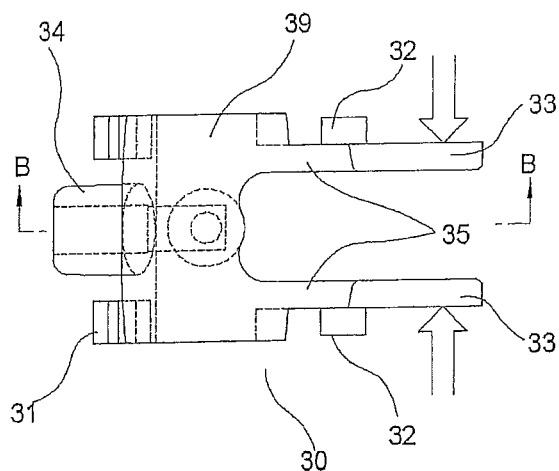
FIG. 9 is a top view of the connector shown in FIG. 8.

The tubing boss 34 defines the attachment arrangement of the tubing 110 by bonding onto the body 39. The first latch tabs 31 are located on each side of the boss 34. FIG. 9 shows how force applied to the outside of release arms 33 bends the arms towards each other. As such, the second latch tabs 32 move closer together so they can pass into the release arm channel 26 of the flexible base 20. Once the bottom 33A of the connector 30 is against surface of the release arm channel 26, removing the force on the release arms 33 allows the second latch tabs 32 to lock into the second receptacle 24 of the flexible base 20. This arrangement provides a strong latching of the connector 30 to the base 20 and, since the tubing does not connect to the side of connector 33 where the release arms 33 are located, it also prevents accidental disconnection by tugging on the tubing 110.

Figure 10:
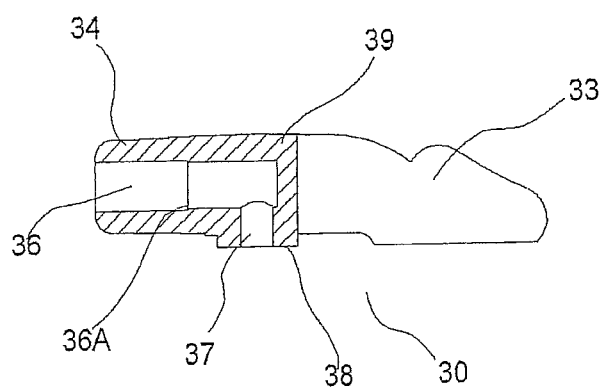
FIG. 10 is a side view of the connector shown in FIG. 8.
Figure 11:
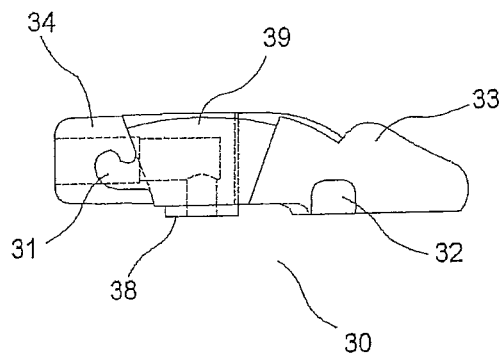
FIG. 11 is another side view of the connector shown in FIG. 8.
Figure 12:
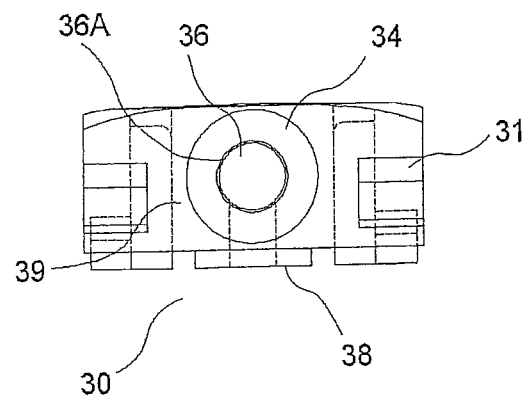
FIG. 12 is a front view of the connector shown in FIG. 8.

FIG. 10 is a cross section of connector 30 showing a tubing bore 36 for receipt of the tubing 110. Step 36A provides a stop for tubing 110 to facilitate assembly. Flow channel 37 connects to bore 36 to complete flow path through body 39 of connector 30.

The tubing 110 is inserted into bore 36 up to step 36A and is bonded in place. Flow channel 37 communicates with bore 36 and sealing surface 38 to provide a sealed flow path through body 39 of connector 30.

The connector 30 is molded from a semi-rigid plastic with spring-like characteristics such as nylon, acetal, PCTA and others. The connector 30 is bonded or glued to the tubing that connects to a medication dispenser. When assembled into the base 20 presses against the one piece sealing cannula 40 and completes the sealed flow path from the medication dispenser to the tip of the cannula 40. The connector 30 utilizes the spring-like properties of the material to permit moving the latching tabs in and out of the mating receptacles in the base.

To engage connector 30 into base 20, the tubing end is tilted with the first latching tabs 31 and tubing 110 slightly down. First latching tabs 31 are inserted into the first receptacle 23 in the base 20. The connector 30 is pivoted downwardly whilst a squeezing force is applied to release arms 33 until bottom surface 33A rests on relief surface 26 in base 20. Releasing the arms 33 allows the second latch tabs 32 to engage the second receptacles 24 and lock connector 30 into base 20.

When compressive force is applied to the release arms 33 of the connector 30 as indicated by the arrows in FIG. 9, the springy hinge areas 35 permit the release arms 33 to bend together, causing the the second latch tabs 32 to move together so they will be able to clear the walls of the release arm channel 26 of the base 20 and permit the connector 30 to pivot down into base 20. When the connector 30 is fully seated in the pocket of the base 20, releasing the force on the release arms 33 causes the second latch tabs 32 to engage second receptacles 24, locking the connector 30 into the base 20.

The cannula 40 is a one piece sealing cannula. The cannula 40 is molded from a flexible material like polyethylene, polypropylene, PTFE, or others. The cannula 40 is integrally formed as one piece. It combines two main functions. The thin stem 45 with the flow conduit is provided to be inserted into the patient to deliver medication to the subcutaneous fat layer. A hub portion of the cannula 45 defines a sealing area 41 at the top of the cannula where a separate seal or o-ring is conventionally used. The hub portion is molded to a desired thickness to provide resilience but in a shape to keep enough flexibility and the ability to conform to the sealing surface of the connector.

Figure 23:
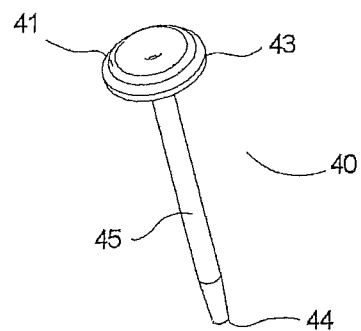
FIG. 23 is an upper perspective view of a cannula shown in FIG. 3.
Figure 24:
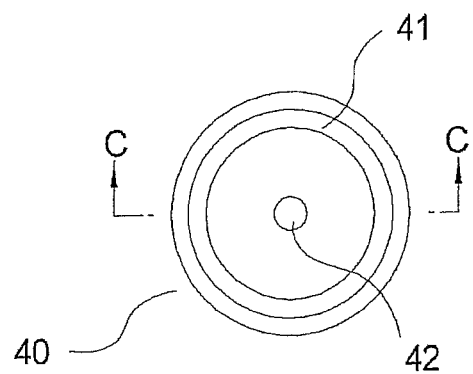
FIG. 24 is a top view of the cannula shown in FIG. 23.

FIG. 23 shows the cannula 40. The cannula 40 comprises the long tubular stem portion 45. The stem portion 45 has a tapered tip 44 at the distal end. The hub portion, acting as the sealing surface 41 is at the medial end of the stem portion 45. The sealing surface 41 has a tapered edge 43, acting as a peripheral edge, around the outer circumference. The tapered edge 43 is configured to lock with the undercut 27A of the base 20. FIG. 24 shows the flow conduit 42 that runs completely through the cannula 40 and allows the medication to flow from the connector 30 through the stem portion 45 of the cannula 40 to the user. An inflow to the flow conduit 42 is defined at the hub portion.

Figure 25:
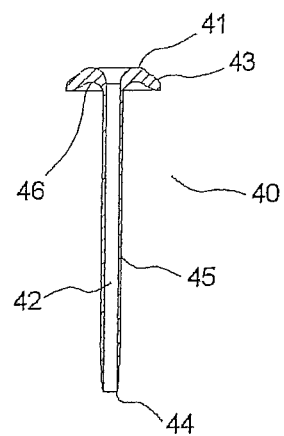
FIG. 25 is a cross-sectional side view of the cannula shown in FIG. 24.

FIG. 25 is a cross-section of the cannula 40 and shows a contour 46, acting as an arched section. The contour 46 allows the sealing surface 41 to flex and conform to the sealing surface 38 of the connector 30. The sealing surface 41 comprises a peak. The peak extends circumferentially about the hub portion. Molding the cannula 40 in one piece with the sealing surface 41 and stem 45 minimises the number of parts needed to make the infusion set and eliminates the need to provide a seal.

The cannula is molded from a material that resists the growth of bacteria or is provided with an anti-microbial additive to the basic resin. The resistance to bacteria allows the patient to use the infusion set longer than the current 3 day limit resulting in significant savings and improvement in comfort to the patient. Changing sets less often reduces the number of sticks, the chance of infection and the irritation of removing the adhesive base.

Tapered edge 43 allows the contour 46 to snap fit with undercuts 27A, 67A and 97A in bases 20, 60 and 90 (see above and below). Contour 46 provides relief below the sealing surface 41 to permit flexing of sealing surface 41 to conform to sealing surface 38, 78, 108 of connectors 30, 70, 100 (see below and above).

Figure 13:
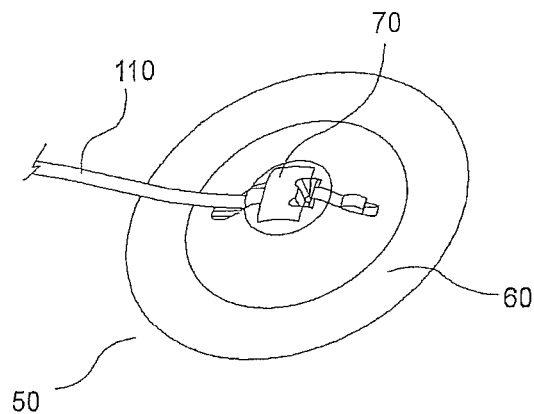
FIG. 13 is an upper perspective view of an alternative assembled infusion set with a connector, a base and a tubing.
Figure 14:
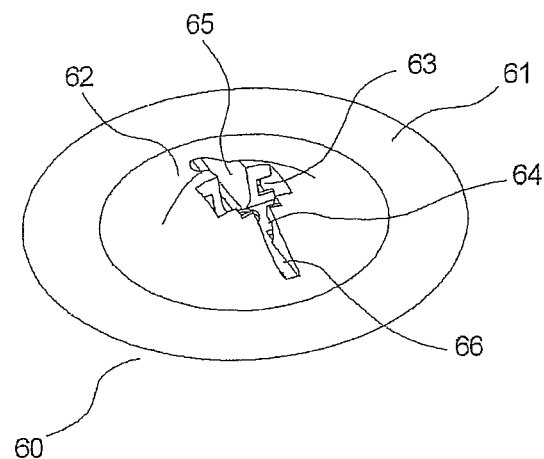
FIG. 14 is an upper perspective view of the base of infusion set shown in FIG. 13.
Figure 15:
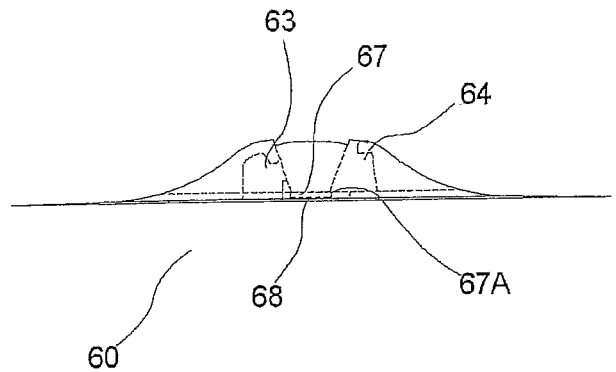
FIG. 15 is a side view of the base shown in FIG. 14.
Figure 16:
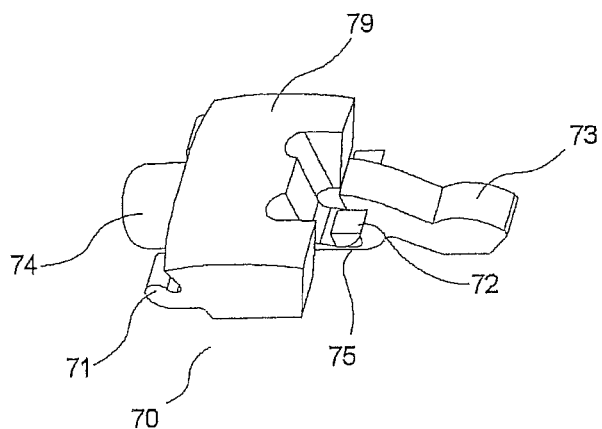
FIG. 16 is an upper perspective view of the connector of the infusion set shown in FIG. 13.

Referring to FIGS. 13 to 17, an alternative embodiment of an infusion set is shown. FIG. 13 shows an assembled alternative infusion set 50. Reference numerals of features of this embodiment correspond to reference numerals of features in FIGS. 1 to 12, but are numbered 40 higher. Corresponding features are not described herein and reference may be made to the above description.

Figure 17:
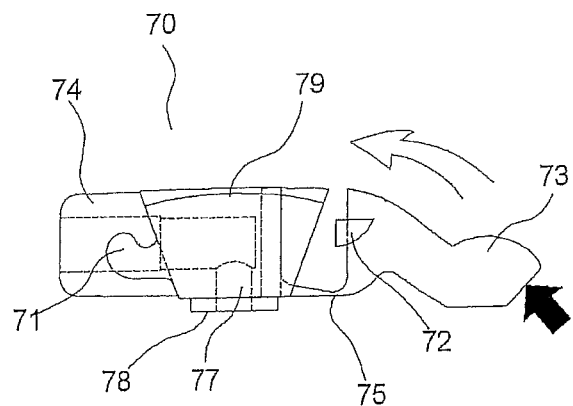
FIG. 17 is a side view of the connector shown in FIG. 16.

This embodiment includes a different arrangement for mounting a connector 70 to a base 60. The connector 70 has a single release arm 73 which bends in an upward manner as shown in FIG. 17. The release arm 73 is a deflectable arm. That is, the arm is deflectable about the body. This movement of the arm 73 rotates the second latch tabs 72 so they will clear the second receptacles 64 of base 60.

The base 60 has thin area 61, acting as a peripheral portion, thick area 62, acting as a central portion. The base 60 also has first receptacle 63 and second receptacle 64. The first receptacle 63 acts as a first latch engaging arrangement. The second receptacle 64 acts as a second latch engaging arrangement. The base also has a tubing channel 65 and release arm channel 66.

Cannula receiving arrangement comprises recess 67. The recess 67 has an undercut 67A to retain tapered edge 43 of cannula 40. Opening 68 allows a stem 45 of cannula 40 to pass through first alternative flexible base 60.

The connector 70 has a first latch tab 71, and a second latch tab 72. Release arm 73 is attached to body 79 by springy hinge area 75.

When force is applied to release arm 73 as shown by the solid arrow, arm 73 bends as shown by the open arrow about the springy hinge area 75. This motion moves the second latching tabs 72 to clear the second receptacle 64 and connect or disconnect with first alternative flexible base 60.

Figure 18:
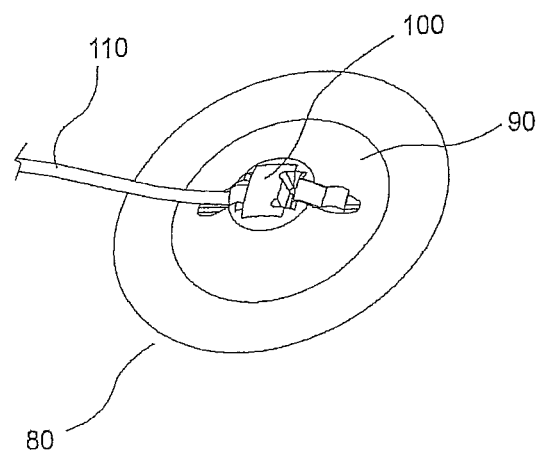
FIG. 18 is an upper perspective view of an alternative assembled infusion set with a connector, a base and a tubing.

An alternative embodiment of an infusion set is shown in FIG. 18. This view shows an assembled alternative infusion set 80. Reference numerals of features of this embodiment correspond to reference numerals of features in FIGS. 1 to 12, but are numbered 70 higher. Corresponding features are not described herein and reference may be made to the above description. The infusion set 80 has a base 90 and a connector 100. Tubing 110 extends from the connector 100.

Figure 19:
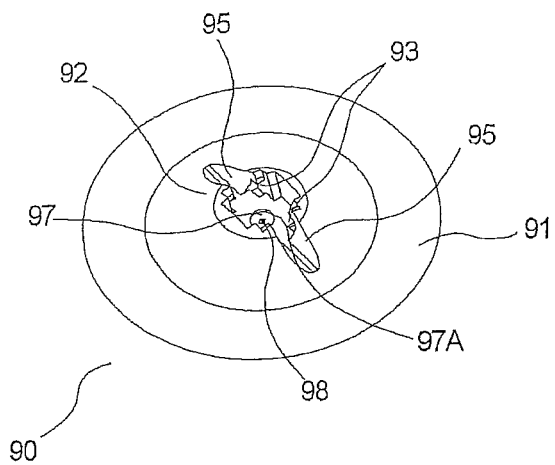
FIG. 19 is an upper perspective view of the base of the infusion set shown in FIG. 18.
Figure 20:
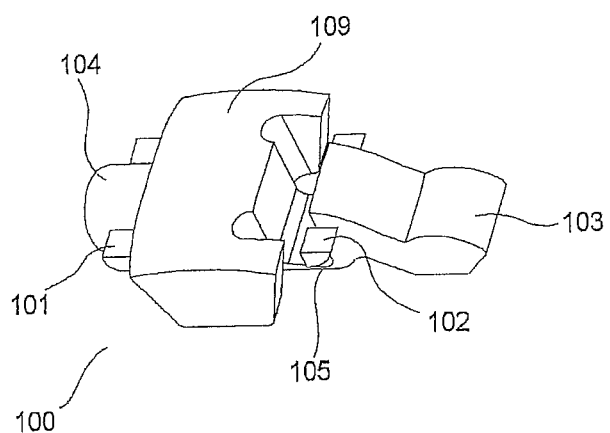
FIG. 20 is an upper perspective view of the connector shown in FIG. 19.
Figure 21:
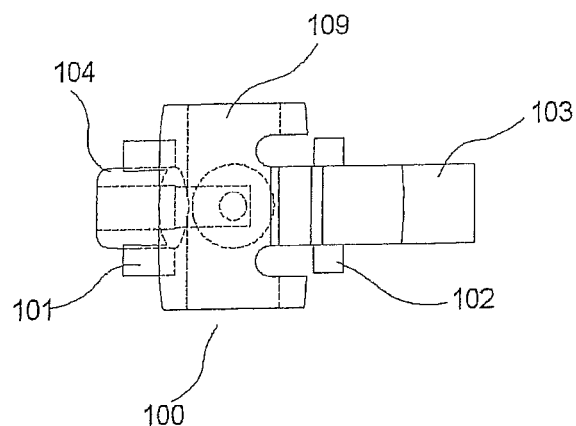
FIG. 21 is a top view of the connector of the connector shown in FIG. 20.
Figure 22:
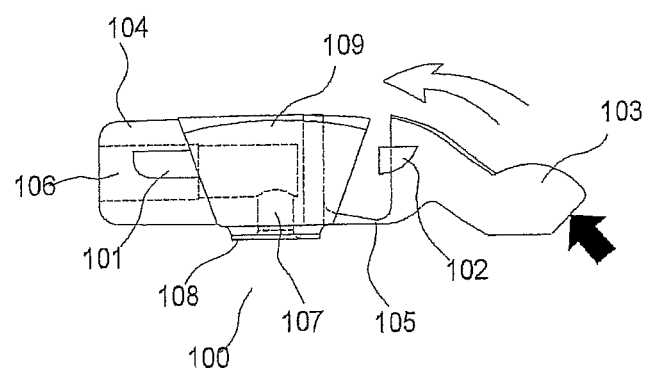
FIG. 22 is a side view of the of the connector of the connector shown in FIG. 20.

Referring now to FIG. 19, the base 90 has a thin area 91, acting as a peripheral portion, and a thick area 92, acting as a central portion. The thin area 91 is a flexible peripheral portion and the thick area 92 is a rigid central portion, although other arrangements are anticipated. Base 90 is symmetrical.

Tubing channel and release arm channel 95 are at least substantially identical. The base 90 has a first receptacle 93 defining a first latch engaging arrangement. The first receptacle 93 comprises two indents defined on either side of the channel 95. The base 90 has a second receptacle 93 defining a second latch engaging arrangement. The second receptacle 93 comprises two indents defined on either side of the channel 95. The first and second receptacles 93, 93 are at least substantially identical and so have been given the same reference number.

The first and second receptacles 93 are disposed on opposing sides of a recess 97. The recess 97 defines the cannula receiving arrangement and is generally the same as described hereinbefore. The recess 97 has undercut 97A.

This symmetry permits insertion of second alternative connector 100 in either direction. That is, the connector 100 is selectably mountable to the base 90 in first and second predetermined mounting orientations.

The connector 100 has tubing boss 104. The connector 100 has a body 109. The body 109 is generally symmetrical. A release arm 103, acting as deflectable arm extends from the body 109. A springy hinge area 105, also known as a resilient hinge member, connects the release arm 103 to the body 109.

The connector 30 has a connecting arrangement for connecting the connector to the base 90. The connecting arrangement comprises first latch tabs 101 and second latch tabs 102. The first latch tabs 101 define a first latch. The second latch tabs 102 define a second latch.

The first latch tabs 101 are on a fixed arm. The fixed arm is fixedly mounted to the body. The second latch tabs 102 are on the deflectable release arm.

The shape of the first latch tabs 101 conforms to the shape of the second latch tabs 102. As such they are interchangably mountable to mounting arrangement of the base 90.

The first latch tabs 101 are equally spaced from the body 109 as second latch tabs 102 when the second latch tabs 102 are in their neutral position relative to the body 109.

In this configuration, the first latch tabs 101 are disposed medially to the same spacing as second latch tabs 102 permitting connector 100 to fit into symmetrical base 90 in either direction. Release arm 103 distends about the body 109 when force is applied.

In the present embodiment, the base 90 is symmetrical. The tubing channel and release arm channel 95 are identical as are the first receptacle and second receptacle 93. This arrangement permits the insertion of the connector 100 in either direction which can be a convenience to the user; both in terms of routing the tubing to the pump and in not having to determine in which direction the insertion must be arranged.

It will be understood that the channels 95 on either side of the cannula receiving arrangement defined by the recess 97 are sized to each accommodate the deflectable arm.

Although in the above described embodiment, the connector 100 is selectably mountable to the base 90 in two predetermined mounting orientations, it will be understood that further configurations are possible. For example, the mounting arrangement may be symmetrical about two axes, such that the connector 100 is selectably mountable to the base 90 in four predetermined mounting orientations.

Figure 26:
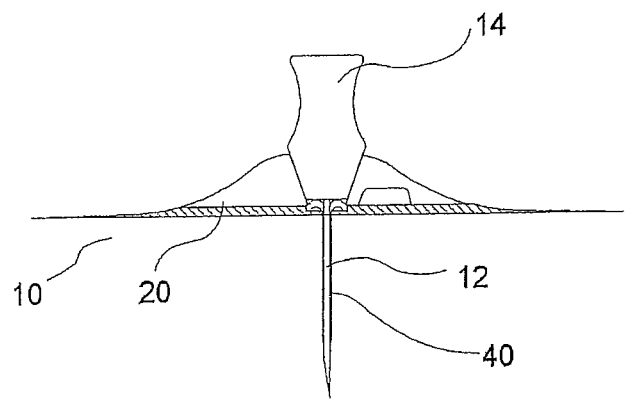
FIG. 26 is a side view of the cannula shown in FIG. 23 engaged with the base, and an introducer arrangement including a needle and a handle.

Referring to FIG. 26, an introducer tool is shown. The introducer tool comprises needle 12 and handle 14.

After the flexible base 20 is attached to the patient's skin, the needle 12 is removed by the handle 14. Next the connector 100 is attached to the base 90 by inserting the first latch tabs 101 into the first receptacle 93. Then the release arm 103 is distended and the connector 30 is rotated down till the bottom surface 103A of the arm 103 rests on the release arm channel 96. In that position the second latch tabs 102 will engage the second receptacle 94 when the pressure is released from the release arm 103. The rotation of the connector 100 also accomplishes another function. It causes the sealing surface 108 of the connector 100 to press on the sealing surface 41 of the cannula 40. This provides an axially directed compression on the hub portion of the cannula 40. This compression action deforms the sealing surface 41 of the cannula 40 and seals the flow conduit 42 of the cannula 40 to the flow channel 37 of the connector 30. The connector 30 is bonded to the tubing 110 which is in turn connected to the infusion pump making a closed flow path from the pump to the patient's subcutaneous fat layer.

The connector may be integrally formed with a delivery device to convey medication to the patient. Delivery devices includes a small pump with reservoir that latches directly to the first and second receptacles. The device could be completely disposable or have a reusable component with disposable connection and reservoir. Even another alternative is to attach a reservoir with a pressurizing component that is activated and controlled by a remote wireless or wired controller.

The infusion set of this invention is a subcutaneous infusion device that is intended to be disposable after one use and is supplied in a sterile and package. The package includes an infusion set and a tubing set. The infusion set has an adhesive with a release paper on the bottom side and a needle in the cannula for insertion into the patient's skin. The needle is removable and is discarded after insertion of the set. The tubing set includes a connector at one end to attach to the infusion pump and another connector at the other end to attach to the base.

The patient uses an alcohol wipe to clean the area of intended insertion of the set. Then opens the package and removes the infusion set. The needle in the base set has a handle for griping the set/needle combination. The patient removes the backing paper from the adhesive side of the set and the needle and then inserts the needle through the skin. Then the base flat area is pressed down against the skin to secure it by the adhesive. The needle is retracted from the set and discarded.

The tubing set is removed from the package and connected to the pump. The pump is then set to prime the tubing. Then the tubing is connected to the base set and the pump delivers the medication as it is programmed.

With the arrangements described above it is possible to simplify the manufacture of the infusion set and to make an infusion set that provides more comfort by better conforming to the patient's skin. It is possible to provide a flexible infusion device for secure and comfortable administration of infused medication.

It is possible to provide an infusion set that conforms to the surface of the patient's skin. It is possible to provide an infusion set that has a secure connection of the delivery tubing set. It is possible to provide an infusion set that has a low profile for convenience and ease of wearing. It is possible to provide an infusion set that uses a pivoting attachment of the tubing set for ease of insertion and low profile.

Although the invention has been described above with reference to one or more preferred embodiments, it will be appreciated that various changes or modifications may be made without departing from the scope of the invention as defined in the appended claims.

The invention claimed is:

1. An infusion set cannula comprising:
   a resiliently deformable hub portion configured to be engaged with a base of an infusion set,
   a stem portion extending from the hub portion,
   wherein the hub portion and the stem portion are integrally formed; and
   wherein the hub portion defines a sealing area and a contour, and wherein the contour allows the sealing area to flex and to conform to a sealing surface of a releasable connector of an infusion set.

2. The infusion set cannula according to claim 1, further comprising a flow conduit defined by the hub portion and the stem portion, wherein an inflow to the flow conduit is defined by the hub portion.

3. The infusion set cannula according to claim 1, wherein the hub portion is configured to seal against the releasable connector to form a flow path through the connector and the cannula.

4. The infusion set cannula according to claim 1, wherein the hub portion comprises a circumferentially extending arched section.

5. The infusion set cannula according to claim 4, wherein the arched section is arched in a radial direction away from an inflow.

6. The infusion set cannula according to claim 4, wherein the arched section comprises a circumferentially extending peak which is configured to deform against the sealing surface of the connector when the arched section is axially compressed.

7. The infusion set cannula according to claim 6, wherein the arched section further comprises a peripheral rim, and the peripheral rim is configured to distend radially outwardly when the arched section is axially compressed.

8. The infusion set cannula according to claim 6, wherein a thickness of the arched section converges from the circumferentially extending peak to a peripheral rim.

9. An infusion set comprising:
   an infusion set base;
   an infusion set cannula having a resiliently deformable hub portion configured to be engaged with the infusion set base and a stem portion extending from the hub portion, wherein the hub portion and the stem portion are integrally formed, and
   an infusion set connector configured to be releasably mounted to the infusion set base;
   wherein the hub portion defines a sealing area and a contour, and wherein the contour allows the sealing area to flex and to conform against the infusion set connector.

10. The infusion set according to claim 9, wherein the infusion set base comprises a recess configured to receive the hub portion of the infusion set cannula, and the infusion set connector comprises a sealing surface, wherein a distance between a base of the recess and the sealing surface when the infusion set is assembled is configured to be less than a thickness of the hub portion.

11. The infusion set according to claim 10, wherein the recess comprises an undercut in a sidewall configured to receive part of the hub portion.

12. The infusion set according to claim 9, wherein the infusion set base comprises a mounting arrangement for mounting the infusion set connector to the base to form a flow path between the connector and the cannula mountable on the base, and wherein the mounting arrangement is configured to engage with the connector to enable the connector to be selectably mounted to the base in at least two predetermined mounting orientations.

13. The infusion set according to claim 9, wherein the infusion set connector comprises a connecting arrangement for mounting the connector to the infusion set base to form a flow path between the connector and the cannula mountable on the base, and wherein the connecting arrangement is configured to engage with the base to enable the connector to be selectably mounted to the base in at least two predetermined mounting orientations.

14. The infusion set according to claim 9, wherein the huh portion is configured to be axially compressed between the base and the connector.

* * * * *